United States Patent [19]
Shealy et al.

[11] Patent Number: 5,242,376
[45] Date of Patent: Sep. 7, 1993

[54] RELAXATION DEVICE AND METHOD

[75] Inventors: C. Norman Shealy, FairGrove; Roger K. Cady, Springfield, both of Mo.

[73] Assignee: 21st Century Holdings, Inc., Longwood, Fla.

[21] Appl. No.: 594,363

[22] Filed: Oct. 9, 1990

[51] Int. Cl.⁵ .............................................. A61M 21/00
[52] U.S. Cl. .................................................... 600/27
[58] Field of Search ..................................... 600/26–27

[56] References Cited

U.S. PATENT DOCUMENTS 4,858,609 8/1989 Cole ..................................... 600/26
4,902,274 2/1990 Gleeson, III .......................... 600/27

FOREIGN PATENT DOCUMENTS 3823402 1/1990 Fed. Rep. of Germany ........ 600/27

OTHER PUBLICATIONS

*Electroencephalography and Clinical Neurophysiology,* "A Device for Generation and Presentation of Modulated Light Stimuli", Richard E. Townsend, 1973, pp. 97–99.

*Primary Examiner*—Lee S. Cohen
*Assistant Examiner*—J. P. Lacyk

[57] ABSTRACT

A light emitting relaxation device and method for placing a subject in a relaxed state. The relaxation device includes a portable mask that has a flashing light source. When the mask is positioned on the subject's head a flashing light, have a preselected color, is emitted into the subject's eyes. The color is selected to increase beta endorphins in the bloodstream of the subject. The mask, preferably, is totally self-contained having built-in controls to set the speed, intensity and duration of the flashing light.

8 Claims, 2 Drawing Sheets

RELAXATION DEVICE AND METHOD

BACKGROUND OF THE INVENTION

This invention relates to a relaxation device and method, and more particularly, to a self-contained portable relaxation device that flashes lights of a predetermined wavelength and a predetermined flashing frequency into the eyes of a subject for a preselected time duration.

Prior art relaxation devices are known which affect the mood of a subject by directing either flashing or colored non-flashing light at the eyes of the subject. The duration that the light is being emitted from the device, as well as the speed at which the light flashes, is set by the subject. The subject places the relaxation device on his head to cover his eyes, the subject closes his eyes, and then light being emitted from the device is directed at the subject's eyes. After a period of time, the subject becomes relaxed and enters into a mood state. These mood states are known as alpha, beta, delta and theta, and correspond to different levels of consciousness and awareness. Examples of these devices, as well as an explanation of the mood state, are disclosed in U.S. Pat. Nos. 4,777,937, 3,722,501, 4,388,928, 4,315,502 and 4,858,609.

A drawback to these prior art devices is that they require connection to an adjacent panel to control the time of the sitting, the flash rate or the color of the light. Such control panels are bulky, expensive, and limit the freedom of movement of the subject during use.

Another drawback to the prior art devices is that they emit white light through a colored filter to provide the subject with different colors. Filters tend to dim the brightness of the light. Thus, a device using filters requires a high intensity white light source. High intensity light sources consume power and therefore are not practical for portable relaxation devices.

SUMMARY OF THE INVENTION

An object of this invention is to provide an improved relaxation device.

Another object of this invention is to direct light into the eyes of a subject having a flashing frequency, wavelength and duration sufficient to increase beta endorphins in the subject's bloodstream.

It is also an object of this invention to direct flashing light of varying durations, amplitude, frequency and color into the eyes of a subject with a completely self-contained device that has switches to control the flashing light parameters.

A further object of this invention is to use a low power light source of a first color that reflects off of a reflector of a second color to generate a third colored light.

An additional object of this invention is to use a portable, self-contained, battery-operated relaxation device to cover the eyes of a subject while directing flashing light into the subject's eyes to allow freedom of movement of the subject during use.

Another object of this invention is to locate control switches on the relaxation device so that the subject can change the relaxation device's settings while the relaxation device is positioned over the subject's eyes.

These and other objects are provided with a relaxation device adapted for placing a subject in a relaxed state, the relaxation device comprising means for emitting light having a first color, and means having a second color different than that of said first color for reflecting said light and directing said reflected light into the eyes of the subject such that the reflected light appears to have a different color than the first color.

Various colors of the spectrum may be directed at the eye without using a filter by reflecting the first color off the second color. Elimination of a filter reduces the power requirement for the light emitting means so as to enable the relaxation device to be battery-operated. The relaxation device also includes means for holding the emitting means and directing means adjacent the eyes of the subject to block light to the eyes not originating from the light emitting means. In a preferred embodiment of the apparatus the first color is red and the second color is blue such that the reflected light appears to the eyes as a shade of purple.

The aforementioned objects are also accomplished with a method for relaxing a subject comprising the steps of providing a source of flashing light having a violet color and directing the violet light at the subject for a predetermined time duration sufficient to increase beta endorphins in the fluid surrounding the brain of the subject. It is recognized that these beta endorphins increase when a light in the violet band flashes at the eyes and has a frequency between 0 and 15 hertz for more than twenty minutes.

In another preferred embodiment a self-containing mask for relaxing a subject and adapted for blocking room light from the subject's eyes is provided, the mask comprises a front portion adapted for covering the eyes of the subject, a light source adapted for providing light to the eyes, the source being flashed at a predetermined frequency, and a power source disposed within the mask and adapted for providing power to the light source. The mask also provides a control means for selecting the predetermined flash frequency of the light provided to the eyes. By including the control means and power source within the mask the subject may change the parameters of the flash frequency without having to remove the mask. In addition, the mask may be used without the subject's freedom of movement being restricted. Alternately, the mask may include means for selecting the intensity of the light source for controlling the time duration of the lights provided to the eyes.

DESCRIPTION OF THE PREFERRED EMBODIMENTS

Figure 1:
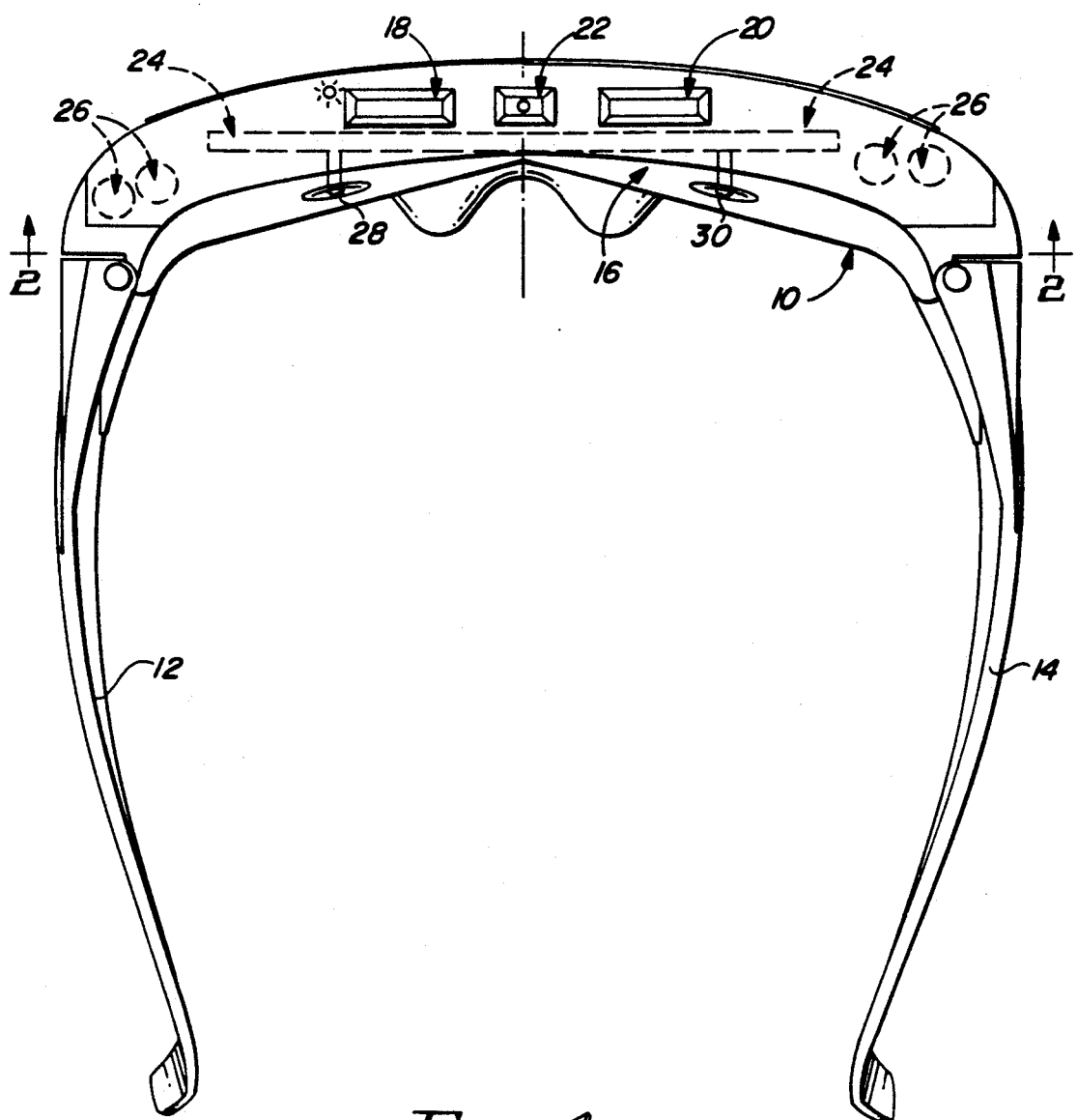
FIG. 1 is a top plan view of the relaxation device in accordance with the invention.

Referring to FIG. 1 there is shown the relaxation device 10, having a left portion 12, right portion 14 and a eye-covering portion, or eye mask 16.

Figure 2:
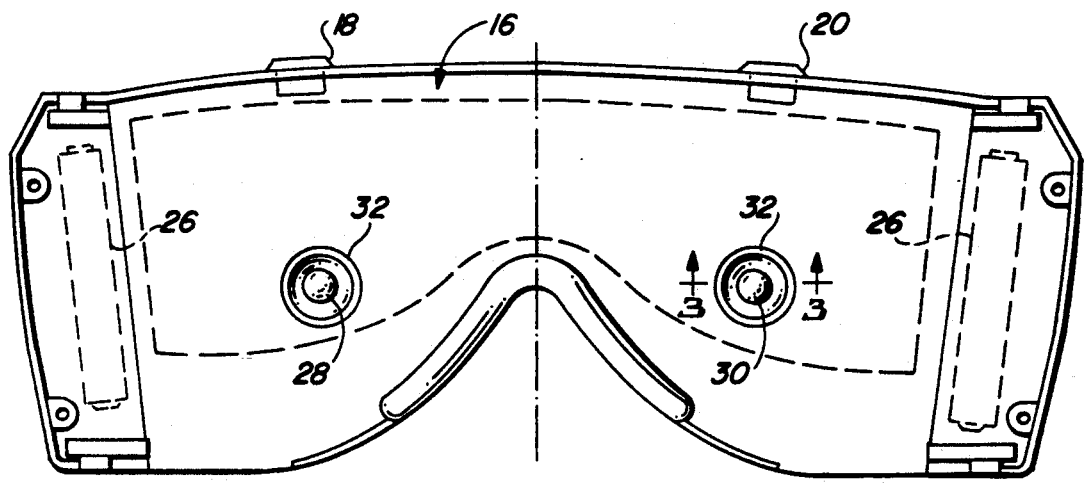
FIG. 2 is a side view of the relaxation device cut along line 2—2 of FIG. 1.

Referring to FIGS. 1 and 2, disposed on the top surface of eye mask 16 is intensity switch 18, flash frequency switch 20 and duration switch 22. Disposed within the mask 16 is circuit board 24 connected to batteries 26 and LEDs 28 and 30. Switches 18, 20 and 22 are also coupled to circuit board 24.

Eye mask 16 is shaped to block light within the room that does not originate from LEDs 28 and 30 from being directed at the subject's eyes. LEDs 28 and 30 project through rear portion 31 and are positioned adjacent to the eyes of the subject when the relaxation device 10 is placed on the head of the subject.

Figure 3:
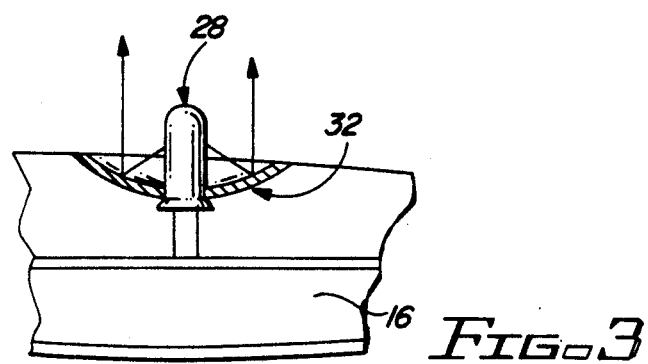
FIG. 3 is a sectioned view of the relaxation device cut along line 3—3 of FIG. 2.

Referring to FIGS. 2 and 3, partially surrounding LED 28 and LED 30 is reflector 32. LEDs 28 and 30 are preferably the color red and reflector 32 is preferably laminated with a blue reflecting material. The wavelength of the red LED 28 and 30 preferably ranges from 650 nm. to 682 nm. Reflector 32 is semi-spherically shaped to direct the light emitted from LED 28 at the subject's eyes. It is recognized that by tinting reflector 32 with a blue color, the red color emitted by LED 28, when seen by the subject, appears as a violet hue.

Intensity switch 18 controls the intensity of LEDs 28 and 30. The flash frequency switch 20 regulates the rate at which LEDs 2 and 30 flash off and on. It is recognized that flashing LEDs 28 and 30 at a frequency of 7.4 hertz and less contributes to the subject entering an theta state, while flashing LEDs 28 and 30 at a frequency above 7.4 hertz contributes to the subject entering a alpha state. The duration that LEDs 28 and 30 flash is regulated with duration switch 22, preferably having three time periods: ten minutes, twenty minutes and forty minutes.

During operation the subject adjusts switches 18, 20 and 22. The subject uses intensity switch 18 to set the intensity of LEDs 28 and 30, uses flash frequency switch 20 to set a mode state and uses duration switch 22 to set the duration that the LEDs 28 and 30 flash. The subject closes his eyes and places the relaxation device 10 on his head with the LEDs 28 and 30 positioned over his eyes. The subject then orients himself in a comfortable position and may elect to listen to music or educational tapes. The subject turns on relaxation device 10 and then, after a predetermined duration of time, the subject may enter an alpha state or a theta state. Further, the subject may change the setting of the switches 18, 20 or 22 without removing eye mask 16. By experimentation and testing the inventor has determined that by having this violet hue flash into the eyes of the subject for a time duration equal to, or exceeding twenty minutes, beta endorphins are increased in the bloodstream of the subject, as well as in the fluid surrounding the subject's brain. It has also been recognized that these beta endorphins are related to the relaxed state or mood of the subject.

Figure 4:
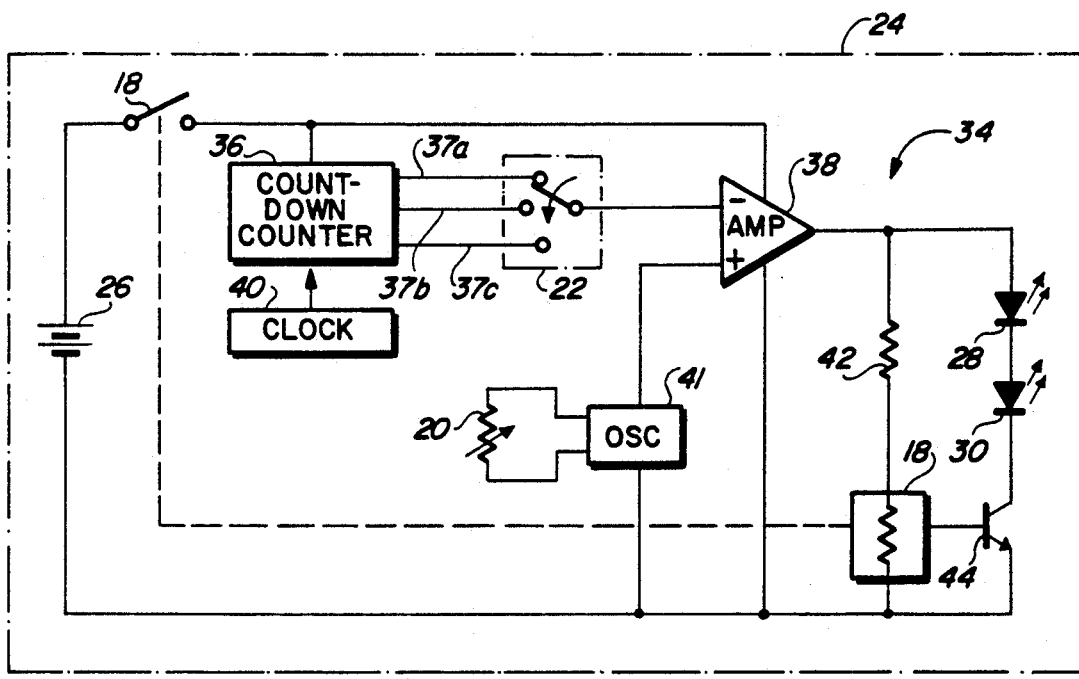
FIG. 4 is a schematic diagram of the electronics of the invention.

Referring to FIG. 4 there is shown a schematic of the circuit 34. Circuit 34 is mounted on circuit board 24 and contains electronics to control the intensity, duration and flash frequency of LEDs 28 and 30. Circuit 34 couples battery 26 through intensity switch 18 to countdown counter 36 and amplifier 38. Countdown counter 36 and amplifier 38 are supplied power from battery 26. Clock 40 feeds a reference timing signal to countdown counter 36. Counter 36 divides the timing signal from clock 40 to provide output signals indicating a predetermined time duration has expired. Clock 40 and counter 36 are selected to provide predetermined time durations of ten, twenty or forty minutes onto terminals 37a, 37b, and 37c, respectively.

Duration switch 22 is positioned on the output terminals 37(a-c) of counter 36 to select the flash duration. The signal on output terminal 37(a-c) is then fed through duration switch 22 to amplifier 38. The voltage level on the output terminals 37(a-c) is normally at a high level until the predetermined time duration of countdown counter 36, coupled to the respective output terminals 37(a-c), has expired. When the time duration expires the output level of the output terminals 37(a-c), corresponding to the output of countdown counter 36 that has expired, is set to a ground or low voltage level.

Oscillator 41 is coupled to amplifier 38. The output voltage of oscillator 41 oscillates at a rate which is set by flash frequency switch 20. Amplifier 38 responds to the output of oscillator 41 and the output of countdown counter 36 being set to a ground level by feeding a flashing output signal to LEDs 28 and 30. Amplifier 38 responds to the output of countdown counter 36 being set to a high voltage level by feeding a low voltage level signal to turn off LEDs 28 and 30. The output of amplifier 38 is also fed through resistor 42 and intensity switch 18 to ground. The output of intensity switch 18 is connected to transistor 44. Intensity switch 18 biases the base of transistor 44 to regulate the current across transistor 44 to control the intensity of LEDs 28 and 30. The intensity of LEDs 28 and 30 preferably ranges from 0 to 1,500 cd/m$^2$.

All the electronics in circuit 34 are placed on a single circuit board 24. This placement allows circuit 34 to be enclosed within relaxation device 10. Enclosing circuit 34 within eye mask 16 allows the relaxation device 10 to be portable without requiring an external power source and control equipment. Further, by constructing eye mask 16 such that batteries 26 are enclosed and control switches 18, 20 and 22 are built-in, relaxation device 10 may easily be programmed by the subject without requiring external control panels. In addition, once the relaxation device 10 is in place on the subject's head, the subject may change settings on control switches 18, 20 and 22 without having to remove relaxation device 10.

This concludes the description of the preferred embodiments. A reading by those skilled in the art will bring t mind various changes without departing from the spirit and scope of the invention. It is intended, however, that the invention only be limited by the following appended claims.

What is claimed is:

1. An apparatus adapted for placing a subject in a relaxed state, the apparatus comprising:
   means for emitting light having a first color;
   means having a second color different than that of said first color for reflecting said light and directing said reflected light into the eyes of a subject such that the reflected light appears to the eyes of the subject to have a different color than said first color; and
   means for holding said emitting means and said reflecting means adjacent the eyes of the subject, and to further block light to the eyes not originating from the emitting means.

2. The apparatus as recited in claim 1 wherein said first color is red, and wherein said second color is blue, such that the reflected light appears to the eyes as a shade of violet.

3. The apparatus as recited in claim 1 wherein said emitting means includes a light emitting diode.

4. The apparatus as recited in claim 1 wherein said reflector is semi-spherically shaped and partially surrounds said light emitting means.

5. A method for placing a subject in a relaxed state comprising the steps of:
   emitting light with a light source having a first color;

reflecting said light off of a reflector having a second color different than that of said first color;

directing said reflected light into the eyes of a subject such that the reflected light appears to the eyes of the subject to have a different color than the said first color; and positioning the light source and reflector adjacent the eyes of the subject, and blocking light from the eyes not originating from the light source.

6. An apparatus adapted for placing a subject in a relaxed state, the apparatus comprising:

a mask having a front portion adapted for covering the eyes of the subject:

means disposed within said front portion for emitting light having a first color, and for flashing the light at a predetermined frequency;

means disposed on said front portion having a second color different than that of said first color for reflecting said light and directing said reflected light at the eyes of the subject such that the reflected light appears to the eyes of the subject to have a different color than said first color;

a power source disposed in said mask and adapted for providing power to the light source;

control means disposed on said mask for selecting the predetermined flash frequency of light; and means for holding said emitting means and said directing means adjacent the eyes within the front portion to block light to the eyes not originating from the light emitting means.

7. A method for relaxing a subject comprising the steps of:

emitting a flashing light having a first color;

reflecting said light at the eyes of the subject, said reflected light having a second color different than said first color, such that the reflected light appears to the eyes of the subject to have a different color than said first color; and providing said reflected flashing light at the eyes of the subject for a predetermined duration sufficient to increase beta endorphins in the fluid surrounding the brain of the subject.

8. The method as recited in claim 7 further comprising the steps of positioning the flashing reflected light adjacent the eyes and blocking any other source of light to the eyes.

* * * * *